United States Patent [19]

Carney et al.

[11] 4,228,093
[45] Oct. 14, 1980

[54] (11Z,13Z)-11,13-HEXADECADIYN-1-OL AND (11Z,13Z)-11,13-HEXADECADIEN-1-OL AND TRIMETHYLSILYL ETHERS THEREOF

[75] Inventors: Robert L. Carney; Clive A. Henrick, both of Palo Alto, Calif.

[73] Assignee: Zoecon Corporation, Palo Alto, Calif.

[21] Appl. No.: 86,233

[22] Filed: Oct. 18, 1979

[51] Int. Cl.³ .......................... C07F 7/18; C07C 33/04
[52] U.S. Cl. .................................... 556/482; 568/873; 568/902; 568/908
[58] Field of Search .................. 260/448.8 R; 568/873

[56] References Cited

U.S. PATENT DOCUMENTS

| 3,031,512 | 4/1962 | Osbond et al. ........................ 568/873 |
| 3,991,125 | 11/1976 | Labovitz et al. ..................... 568/873 |
| 3,996,270 | 12/1976 | Friedman et al. ............... 568/873 X |
| 4,163,021 | 7/1979 | Cohen et al. ............. 260/448.8 R X |
| 4,180,682 | 12/1979 | Cohen et al. ............. 260/448.8 R X |
| 4,189,614 | 2/1980 | Samain et al. ............ 260/448.8 R X |

Primary Examiner—Paul F. Shaver

[57] ABSTRACT

Synthesis of an attractant (11Z,13Z)-11,13-hexadecadienal for the navel orangeworm *Amyelois transitella*, and intermediates therefor.

3 Claims, No Drawings

(11Z,13Z)-11,13-HEXADECADIYN-1-OL AND (11Z,13Z)-11,13-HEXADECADIEN-1-OL AND TRIMETHYLSILYL ETHERS THEREOF

This invention relates to the synthesis of an attractant for the navel orangeworm, *Amyelois transitella*, and intermediates.

The compound (11Z,13Z)-11,13-hexadecadienal has been found to be an effective attractant for the navel orangeworm, which is a serious agricultural pest, particularly for almond growers. The foregoing compound has been reported to be the sex pheromone of the female navel orangeworm.

The present invention provides means for the synthesis of (11Z,13Z)-11,13-hexadecadienal and intermediates therefor.

The synthesis of the present invention can be outlined as follows:

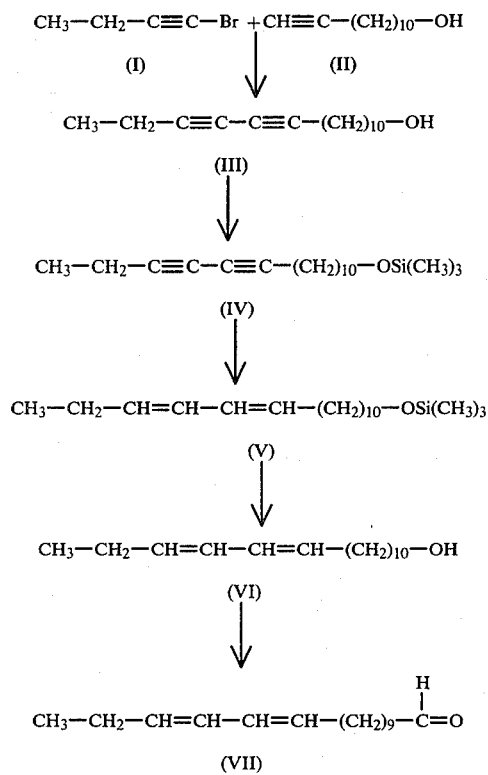

In the practice of the above-outlined synthesis, 1-bromo-1-butyne (I) is alkylated with 11-dodecyn-1-ol (II) using the Cadiot-Chodkiewicz coupling as described by L. Brandsma, *Preparative Acetylenic Chemistry*, Elsevier Publishing Co., Amsterdam, New York (1971), to yield (11Z,13Z)11,13-hexadecadiyn-1-ol (III). The enynol (III) is converted to its trimethylsilyl ether (IV) using chlorotrimethylsilane and triethylamine, then is treated with dicyclohexylborane in tetrahydrofuran followed by acetic acid to yield the trimethylsilyl ether of (11Z,13Z)-11,13-hexadecadien-1-ol (V). The ether (V) is converted to the corresponding alcohol (VI) by reaction with trichloroacetic acid in ethanol, after which it is oxidized to the desired aldehyde, (11Z,13Z)-11,13-hexadecadien-1-al (VII), using chromic acid and pyridine.

The bromobutyne (I) can be prepared as described by C. A. Henrick, "The Synthesis of Insect Sex Pheromones", Tetrahedron Report No. 34, Pergamon Press Ltd., Oxford, England (1978); Tetrahedron 33, 1845 (1977).

The attractant prepared by the present invention can be used in conjunction with insect traps as part of an integrated pest management program for detection of the navel orangeworm and determination of the need to apply pesticides. The attractant is active at very low levels of the order of 100 to 1,000 micrograms per trap. The attractant can be used by charging a small polyethylene cap or rubber septa which is then placed in a sticky trap.

The following examples are provided to illustrate the practice of the invention. Temperature is given in degrees Centigrade.

EXAMPLE 1

To a mixture of 11-dodecyn-1-ol (286 mmol), copper chloride (0.572 g), hydroxylamine hydrochloride (1.15 g), methanol (57 ml) and water (34.5 ml) is slowly added, at 0°, is added a 70% aqueous solution of ethyl amine (46 ml). The mixture is warmed to room temperature and 1-bromo-1-butyne (114.5 mmol) is added at such a rate that the temperature is maintaned at 27°-30°. Stirring is continued for 1 hour. The product is worked up by adding sodium cyanide and water and extracting with ether (4X). The combined extracts are washed with water and with brine, dried over magnesium sulfate and the solvent is then removed in vacuo to yield (11Z,13Z,)-11,13-hexadecadiyn1-ol.

The (11Z,13Z)-11,13-hexadecadiyn-1-ol (21.2 mmol) is combined with chlorotrimethylsilane (23.4 mmol), triethylamine (23.4 mmol) and dichloromethane (20 ml), and the mixture is left at room temperature, under nitrogen, for 4 hours. The resulting reaction mixture is diluted with pentane and filtered. The filtrate is concentrated and again diluted with pentane and filtered. Removal of solvent and purification of the crude product gives the trimethylsilyl ether of (11Z,13Z)-11,13-hexadecadiyn-1-ol.

EXAMPLE 2

To a solution of cyclohexene (65.5 mmol) in 20 ml of dry tetrahydrofuran is added, at $-5°$ to $0°$, a solution of borane (1 M, 32.7 mmol) in tetrahydrofuran. The white precipitate is stirred at $0°-5°$ for 1 hour. To the dicyclohexylborane is added a solution of the trimethylsilyl ether of (11Z,13Z)11,13-hexadecadiyn-1-ol (26.2 mmol) in tetrahydrofuran, keeping the temperature at $-5°$ to $0°$. The reaction mixture is then allowed to come to room temperature and left for 5 hours. More dicyclohexylborane is added (16.4 mmol) at $-5°$ to $0°$, and the mixture is stirred overnight at room temperature. Glacial acetic acid (12 ml) is added to the resulting solution, which is heated for 20 hours. The reaction mixture is oxidized with 40 ml of 6N NaOH and 14 ml of 30% $H_2O_2$ at $30°-35°$ for one-half hour, after which it is saturated with NaCl. The organic layer is separated and the aqueous phase is extracted with pentane (2X). The organic phases are combined and dried over magnesium sulfate and the solvent is removed to yield the trimethylsilyl ether of (11Z,13Z)-11,13-hexadecadien-1-ol.

The product above is stirred with 10 g of trichloroacetic acid in 60 ml of ethanol and 30 ml of water. After the reaction is complete, the solution is neutralized with 3N NaOH and extracted with pentane. After drying over magnesium sulfate, the pentane is removed under vacuum to give (11Z,13Z)-11,13-hexadecadien-1-ol.

EXAMPLE 3

(11Z,13Z)-11,13-hexadecadien-1-ol (3.19 mmol) and acetic anhydride (6.38 mmol), in 5 ml of dry pyridine, are stirred under nitrogen at room temperature for 20 hours. The reaction mixture is then poured in sodium bicarbonate solution and extracted with pentane (2X). The organic layer is washed with dilute HCl and with brine, dried over magnesium sulfate and the solvent removed in vacuo. The crude product is purified to yield the final product, (11Z,13Z)-11,13-hexadecadien-1-al.

What is claimed is:

1. The compound, (11Z,13Z)-11,13-hexadecadyin-1-ol, and the trimethylsilyl ether thereof.
2. The compound, (11Z,13Z)-11,13-hexadecadiyn-1-ol, according to claim 1.
3. The compound, the trimethylsilyl ether of (11Z,13Z)-11,13-hexadecadien-1-ol.